United States Patent [19]

Onopchenko et al.

[11] 4,104,281

[45] Aug. 1, 1978

[54] PROCESS FOR PREPARING NOVEL ISOMERIC DICARBOXY, DI (HYDROXYMETHYL) DIPHENYLMETHANE DILACTONES

[75] Inventors: Anatoli Onopchenko, Monroeville; Johann G. Schulz, Pittsburgh; Edward T. Sabourin, Allison Park, all of Pa.

[73] Assignee: Gulf Research & Development Company, Pittsburgh, Pa.

[21] Appl. No.: 748,686

[22] Filed: Dec. 8, 1976

[51] Int. Cl.$^2$ .................. C07D 307/88; C07D 407/10
[52] U.S. Cl. ............................ 260/343.3 R; 528/341; 528/354
[58] Field of Search .................................. 260/343.3 R

[56] References Cited

U.S. PATENT DOCUMENTS

| 2,079,325 | 5/1937 | Larchar et al. .................... 260/343.3 |
| 3,332,964 | 7/1967 | McCraken et al. ................ 260/346.3 |
| 3,895,037 | 7/1975 | Onopchenko et al. ........... 260/346.3 |

*Primary Examiner*—Natalie Trousof
*Assistant Examiner*—Jane T. Fan

[57] ABSTRACT

A process for preparing novel isomeric dicarboxy, di (hydroxymethyl), diphenylmethane dilactones wherein benzophenone-3, 4,3′,4′-tetracarboxylic dianhydride is subjected to hydrogenation in an ether or ester carrier in the presence of a hydrogenation catalyst pretreated in an ether carrier.

11 Claims, No Drawings

PROCESS FOR PREPARING NOVEL ISOMERIC DICARBOXY, DI (HYDROXYMETHYL) DIPHENYLMETHANE DILACTONES

BACKGROUND OF THE INVENTION

1. Field of the Invention

This invention relates to a process for preparing novel isomeric dicarboxy, di(hydroxymethyl), diphenylmethane dilactones wherein benzophenone-3,4,3',4'-tetracarboxylic dianhydride is subjected to hydrogenation in an ether or ester carrier in the presence of a hydrogenation catalyst pretreated in an ether carrier.

2. Description of Prior Art

Hydrogenation of BTDA, or of derivatives thereof, has been carried out in U.S. Pat. Nos. 3,332,964 and 3,895,037, but in neither case was a process disclosed or taught resulting in the novel isomeric dicarboxy, di(hydroxymethyl), diphenylmethane dilactones claimed herein.

SUMMARY OF THE INVENTION

In the novel process disclosed and claimed herein benzophenone-3,4,3',4'-tetracarboxylic dianhydride (BTDA) is subjected to hydrogenation in an ether or ester carrier in the presence of a hydrogenation catalyst pretreated in an ether carrier to obtain the following novel isomeric dicarboxy, di(hydroxymethyl), diphenylmethane dilactones:

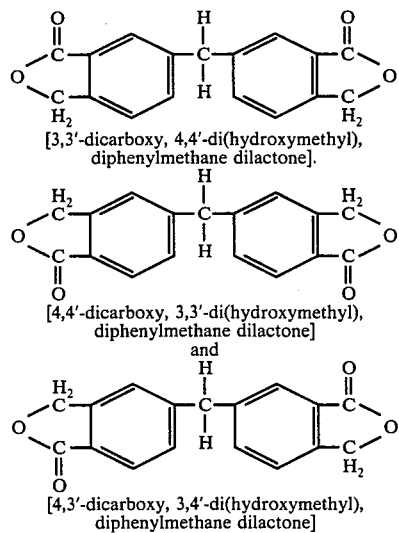

[3,3'-dicarboxy, 4,4'-di(hydroxymethyl), diphenylmethane dilactone].

[4,4'-dicarboxy, 3,3'-di(hydroxymethyl), diphenylmethane dilactone]
and

[4,3'-dicarboxy, 3,4'-di(hydroxymethyl), diphenylmethane dilactone]

BRIEF DESCRIPTION OF THE PROCESS AND NOVEL COMPOUNDS

As noted, the charge to be hydrogenated herein is benzophenone-3,4,3',4'-tetracarboxylic dianhydride. It is critical, however, in order to convert BTDA, by hydrogenation, to the specific dicarboxy, di(hydroxymethyl), diphenylmethane dilactones claimed herein that the hydrogenation catalyst used in said conversion, for example, nickel, be subjected to the specific pretreatment described herein prior to said conversion.

This pretreatment is carried out by heating the catalyst in a hydrogen atmosphere while maintaining the same in a critical carrier, namely, an ether, for example, tetrahydrofuran or p-dioxane. Thus the catalyst is placed in the ether carrier and the resultant slurry is stirred while maintaining a temperature of about 165° to about 230° C., preferably about 180° to about 200° C., and a hydrogen pressure of about 300 to about 2000 pounds per square inch gauge (about 20 to about 136 kilograms per square centimeter), preferably about 600 to about 1500 pounds per square inch gauge (about 40 to about 102 kilograms per square centimeter), for about 10 minutes to about three hours, preferably about 0.5 to about one hour. The amount of ether used can vary over a wide range, but can be, for example, in a weight range of about 1000:1 to about 3:1, preferably about 25:1 to about 5:1, relative to the catalyst. At the end of this period the carrier and catalyst can be separated from each other by any convenient means, for example, filtration.

The hydrogenation step is carried out in the same manner as the catalyst pretreatment step defined above, except that in addition to the carrier, BTDA is also present and the carrier used can be either the same ether used during said pretreatment or an ester. If the same ether is used in the pretreatment and in the hydrogenation steps, then, obviously, there is no need to separate the catalyst and ether from each other at the end of the pretreatment step and the only requirement is that the BTDA to be hydrogenated be added to the slurry.

The ester to be used in the hydrogenation stage, if an ether is not used, can be defined by the formula

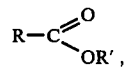

wherein R and R', the same or different, can be alkyl groups having from one to 10 carbon atoms, preferably from two to six carbon atoms, or aryl groups having from six to 12 carbon atoms, preferably six to eight carbon atoms. Specific examples of esters that can be used include ethyl acetate, methyl acetate, dimethyl malonate, cyclohexyl propionate, phenylbutyrate, etc.

As in the pretreatment step defined above, the slurry containing the carrier, catalyst and BTDA is contacted while stirring and heating in an atmosphere of hydrogen, resulting in the hydrogenation of the BTDA to the specific novel dilactones. The temperature can be in the range of about 165° to about 230° C., preferably about 180° to about 200° C., the hydrogen pressure about 300 to about 2000 pounds per square inch gauge (about 20 to about 136 kilograms per square centimeter), preferably about 600 to about 1500 pounds per square inch gauge (about 40 to about 102 kilograms per square centimeter), and the reaction time about five minutes to about 10 hours, preferably about 15 minutes to about three hours. The amount of carrier used can be in the same range as in the catalyst pretreatment step.

At the end of the reaction the desired dilactones are recovered from the reaction mixture by cooling to a temperature of about −20° to about 45° C., preferably room tempterature, and depressuring to atmospheric pressure. The resulting product solution is filtered to remove catalyst and any unreacted BTDA. The filtrate is concentrated by heating at a temperature of about 30° to about 150° C., preferably about 40° to about 100° C., and a vacuum of about five to about 100 inches of mercury by removing from about 10 to about 100 weight percent, preferably about 25 to about 70 weight percent of the carrier therefrom. As a result of such concentration, the desired and novel dilactones crystallize out of solution and are recovered, for example, by filtration, in situations wherein not all carrier is removed. When all of the carrier is removed, however, the solid crystalline material remaining is composed of the novel dilactones.

DESCRIPTION OF PREFERRED EMBODIMENTS

A number of runs was carried out wherein BTDA was subjected to hydrogenation with a nickel catalyst (NiO104P, manufactured by Harshaw Chemical Company, Cleveland, Ohio). In each of Runs Nos. 2, 3, 4, 5, 7, 8 and 9, reported below, the catalyst was pretreated by heating, while stirring, a slurry containing the catalyst and a carrier in a hydrogen atmosphere in a one-liter autoclave. In Runs Nos. 1 and 6 the catalyst was not pretreated. In the runs wherein the carrier in the pretreatment step and in the subsequent hydrogenation were not the same, the mixture, after pretreatment, was cooled to room temperature and depressured to atmospheric pressure and filtered to recover the catalyst, and the catalyst, a carrier different from the first, and BTDA were placed in a one-liter autoclave. When the same carrier was used in both stages, the reaction mixture was merely cooled to room temperature and depressured to atmospheric pressure and BTDA was added thereto. In each case the slurry containing the carrier, BTDA and catalyst were stirred and heated in a hydrogen atmosphere.

and 9, determinations were made for melting point, neutral equivalent and for carbon and hydrogen analysis of each of the recovered crystalline products. In each of Runs Nos. 5 and 6 hydrogenation resulted in the production of a complex, non-resolvable, tacky, glass-like product.

Run No. 1 was a duplicate of Run No. V in U.S. Pat. No. 3,895,037 referred to above. In this run the filtrate recovered was evaporated to a volume of 250 milliliters, but only a few crystals were formed along the edges of the container. The mixture was then transferred to a one-liter round-bottomed flask, employing 100 milliliters of acetone as wash solvent, and then concentrated to a volume of 200 milliliters. The product solidified to a glass-like finish, but was viscous and tacky. An attempt was made to recrystallize the product from ethyl acetate solution. After standing for eleven days some crystallization of product occurred, but filtration did not result in the recovery of solids. The product, amounting to 143.8 grams, was permitted to stand an additional three days, resulting in the formation of but 3.2 grams of a white solid, which was recovered by filtration. Its melting point was determined to be in the range of 185° to 241° C. and its neutral equivalent 112. The conditions used in the runs are summarized in Table I below and the results obtained in Table II.

TABLE I

| Run No. | Reactants, Gms. | | | Catalyst Pretreatment | | | | | | |
|---|---|---|---|---|---|---|---|---|---|---|
| | BTDA | Ni | Carrier (Ml.) | Carrier(Ml.) | Temp., ° C. | $H_2$, PSIG | Time, Minutes | Temp., ° C. | $H_2$, PSIG | Time, Minutes |
| 1 | 150 | 15 | Tetrahydrofuran(500) | ← | None | → | → | 200 | 1050 | 30 |
| 2 | 150 | 15 | Tetrahydrofuran(500) | Tetrahydrofuran(500) | 190 | 1000 | 30 | 200 | 1050 | 30 |
| 3 | 150 | 20 | Ethyl Acetate(500) | Tetrahydrofuran(500) | 190 | 1000 | 30 | 200 | 1050 | 30 |
| 4 | 40 | 20 | Ethyl Acetate(500) | Tetrahydrofuran(500) | 200 | 1000 | 30 | 200 | 1050 | 40 |
| 5 | 40 | 20 | Ethyl Acetate(500) | Ethyl Acetate(500) | 190 | 1000 | 45 | 200 | 1050 | 30 |
| 6 | 40 | 20 | Ethyl Acetate(500) | ← | None | → | → | 200 | 1500 | 30 |
| 7 | 40 | 20 | Ethyl Acetate(500) | P-Dioxane(500) | 190 | 1000 | 30 | 200 | 1500 | 45 |
| 8 | 40 | 20 | P-Dioxane(500) | P-Dioxane(500) | 190 | 1000 | 30 | 200 | 1500 | 45 |
| 9 | 80 | 20 | Diphenyl Ether(500) | Tetrahydrofuran(500) | 190 | 1000 | 30 | 180 | 1500 | 60 |

TABLE II

| Run No. | Solids Formed, Grams | BTDA Converted, Per Cent | Yield of Dilactones | Melting Point, ° C. | Neutral Equivalent |
|---|---|---|---|---|---|
| 1 | 3.2 | 100 | 2.5 | 185–241 | 112 |
| 2 | 54.8 | 50 | 42 | 182–184 | 145 |
| 3 | 67.8 | 65 | 52 | Not taken* | Not taken* |
| 4 | 29.5 | 100 | 85 | Not taken* | Not taken* |
| 5 | None | 100 | (Complex, non-resolvable, tacky, glass-like product) | | |
| 6 | None | 100 | | | |
| 7 | 26 | 100 | 75 | Not taken* | Not taken* |
| 8 | 23.6 | 100 | 68 | Not taken* | Not taken* |
| 9 | 28.5 | Not taken | 41 | 197–213 | 137.5 |

*Course of reaction was monitored by spectral (IR and NMR) data.

The recovery procedures employed varied with the products obtained. In Runs Nos. 2, 3, 4, 7, 8 and 9 the autoclave at the end of the hydrogenation period was cooled to room temperature and depressured to atmospheric pressure and the contents thereof were filtered to separate catalyst and any unreacted BTDA therefrom. In Runs Nos. 2, 3, 4, 7 and 8 the filtrate was then concentrated from about one-third to about one quarter of its volume by heating in a rotary evaporator, while in Run No. 9 crystallization occurred without concentration of filtrate. In each case, however, the resultant filtrate was filtered to recover crystalline product. In Run No. 2 the crystalline product that was recovered was twice crystallized from ethyl acetate to recover a purer dilactone product. In each of Runs Nos. 2, 3, 4, 7 and 8, NMR and IR studies of the recovered crystalline products disclosed the presence of the three novel isomeric dilactones claimed herein. In each of Runs Nos. 2

As noted, in addition to the data in Table II, carbon and hydrogen analysis was determined for the crystalline products obtained in Runs Nos. 2 and 9. For the novel dilactones claimed herein, $C_{17}H_{12}O_4$, the theoretical weight percent carbon is 72.85 percent and for hydrogen 4.32 weight percent. Analysis for the products in Runs Nos. 2 and 9 showed 72.42 and 72.85 percent, respectively, for carbon and 4.50 and 4.40, respectively, for hydrogen, substantially in agreement with the respective theoretical values. The theoretical neutral equivalent for the novel dilactones herein is 140. Several attempts were made to determine the isomeric composition of the dilactones produced herein using gas chromatography, but without success. Therefore, a sample of the product was subjected to hydrogenolysis following the procedure of N. Finch et al in the Journal of Organic Chemistry, Volume 41, No. 15, page 2509

(1976), resulting in an acidic product having a neutral equivalent of 158.6 and a melting point range of 50°–82° C. (theoretical neutral equivalent = 142). Gas chromatographic analysis of the dimethyl, diphenylmethane, dicarboxylic acids gave three major components in 20.9, 43.5 and 35.6 weight percent, respectively, in order of their appearance on the chromatogram, accounting for over 95 percent of the total product. No attempts were made to determine which peak on the chromatogram corresponded to which isomer. The products of the hydrogenolysis are the following: 3,3'-dimethyl-4,4'-dicarboxydiphenylmethane, 3,3'-dicarboxy-4,4'-dimethyldiphenylmethane and 3,4'-dimethyl-4,3'-dicarboxydiphenylmethane, each corresponding to the respective dilactone isomer. To show that no unusual rearrangements occurred during dilactone preparation, a portion of the product was oxidized with 25 percent nitric acid at 175°–180° C., resulting in a recovery of 79 percent yield of a known 3,4,3',4'-benzophenone tetracarboxylic acid, identical in all respects to the authentic sample. The neutral equivalent of Run No. 2 was 145, substantially in agreement with theoretical. The neutral equivalent for the product of Run No. 9 was 137.5, in good agreement with the theoretical. Since the NMR and IR results in Runs Nos. 3, 4, 7 and 8 were similar to those of Run No. 2, it was not believed necessary to verify further that the dilactones obtained in each instance were the same as those of Run No. 2.

The procedures of Runs Nos. 1, 5 and 6, which fall outside the scope of the claimed invention, are shown not to result in the production of the novel dilactones claimed herein. Thus, in Run No. 1, wherein no pretreatment of the catalyst took place, only 3.2 grams of product were obtained. A melting point ranging from 185° to 241° C. shows the presence of many compounds in the mixture. The neutral equivalent of 112 was far below the theoretical neutral equivalent of the novel dilactones, 140. In Run No. 5 wherein pretreatment of catalyst was not conducted in an ether solvent, but rather ethyl acetate, the desired dilactones were not obtained. In Run No. 6 wherein no pretreatment of catalyst was conducted and even though an ester was used during hydrogenation, the desired dilactones were not obtained.

The novel isomeric dilactones of this invention can be used in various conventional applications that are well known for gamma lactones, including phthalides, for example, in the preparation of insecticides, fungicides, perfume flavoring, preparation of copolymers using trioxane and phthalide, as, for example, in U.S. Pat. No. 3,026,299, etc. The novel dilactones herein are especially attractive, because they are difunctional and thus can react on both ends of the molecule with, for example, trioxane, diamines, isocyanates, etc., to form long chain polymeric materials of high tensile strength which can be drawn into fibers that can be woven into cloth. This is shown for example in the following.

EXAMPLE I

A total of 28 grams of a mixture of dilactones prepared in accordance with the procedure of Run No. 2, and six grams of ethylene diamine were charged into a flask containing 100 milliliters of N-methylpyrollidine and 5 grams of benzene. The flask was fitted with a Dean-Stark trap filled with 50 milliliters of benzene. The reaction mixture was heated under reflux (around 140° C.) for 4.5 days. A total of 4.3 grams of water was collected. After stripping off N-methylpyrollidine under reduced pressure, the residue amounted to 30.2 grams. The crude polymer was ground into power, washed several times with about 100-milliliter portions of boiling isopropanol to remove last traces of solvent and air dried for six hours, followed by drying in a vacuum at 100° C. for 10 hours. Analysis of the product indicated the reaction proceeded as follows:

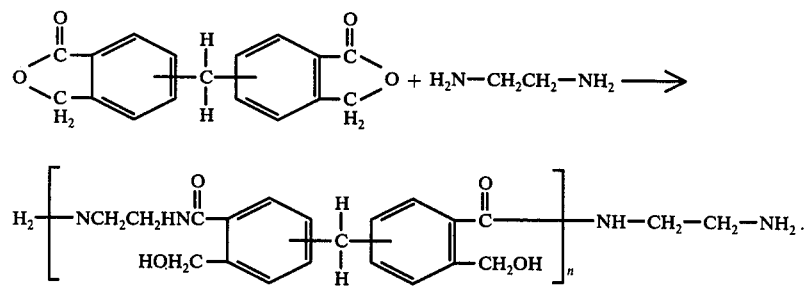

The resin was found to have a molecular weight in excess of 10,000 and distinguished itself by its virtual insolubility in conventional solvents, such as methanol, acetone, ethyl acetate, tetrahydrofuran and benzene. The molten resin was drawn into flexible fibers capable of being cold drawn to impart additional mechanical strength thereto suitable for the preparation of fabrics therefrom.

Obviously, many modifications and variations of the invention as hereinabove set forth can be made without departing from the spirit and scope thereof, and therefore only such limitations should be imposed as are indicated in the appended claims.

We claim:

1. A process for converting benzophenone-3,4,3',4'-tetracarboxylic dianhydride to dicarboxy, di(hydroxymethyl), diphenylmethane dilactones which comprises subjecting said benzophenone-3,4,3',4'-tetracarboxylic dianhydride to hydrogenation in a hydrogen atmosphere using an ether or ester carrier in the presence of nickel pretreated in a hydrogen atmosphere using an ether solvent.

2. The process of claim 1 wherein the carrier used during the hydrogenation step is tetrahydrofuran.

3. The process of claim 1 where the carrier used during the hydrogenation step is p-dioxane.

4. The process of claim 1 wherein said ether is tetrahydrofuran.

5. The process of claim 1 wherein said ether is p-dioxane.

6. The process of claim 1 wherein said ester is defined by the formula:

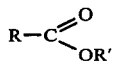

wherein R and R' can be alkyl groups having from one to 10 carbon atoms or aryl groups having from six to 12 carbon atoms.

7. The process of claim 6 wherein R and R' can be alkyl groups having from two to six carbon atoms or aryl groups having from six to eight carbon atoms.

8. The process of claim 6 wherein said ester is ethyl acetate.

9. The process of claim 1 wherein the temperature of the reaction is in the range of about 165° to about 230° C. and the pressure about 300 to about 2000 pounds per square inch gauge.

10. The process of claim 1 wherein the temperature of the reaction is in the range of about 180° to about 200° C. and the pressure about 600 to about 1500 pounds per square inch gauge.

11. A mixture containing the following three isomeric dilactones: 3,3'-dicarboxy, 4,4'-di(hydroxymethyl), diphenylmethane dilactone, 4,4'-dicarboxy, 3,3'-di(hydroxymethyl), diphenylmethane dilactone and 4,3'-dicarboxy, 3,4'-di(hydroxymethyl), diphenylmethane dilactone.

* * * * *